(12) United States Patent
Wang et al.

(10) Patent No.: US 7,041,784 B2
(45) Date of Patent: May 9, 2006

(54) APOPTOTIC COMPOUNDS

(75) Inventors: Xiaodong Wang, Dallas, TX (US); Chunying Du, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 251 days.

(21) Appl. No.: 10/641,539

(22) Filed: Aug. 15, 2003

(65) Prior Publication Data
US 2004/0077542 A1   Apr. 22, 2004

Related U.S. Application Data

(63) Continuation of application No. 09/645,075, filed on Aug. 23, 2000, now Pat. No. 6,608,026.

(51) Int. Cl.
*A61K 38/00* (2006.01)

(52) U.S. Cl. .................. 530/300; 530/317; 530/326
(58) Field of Classification Search .............. 514/2, 514/9–17; 530/300, 317, 326–331; 435/7.1
See application file for complete search history.

(56) References Cited

U.S. PATENT DOCUMENTS

| | | | |
|---|---|---|---|
| 5,492,894 A | 2/1996 | Bascom et al. | |
| 6,110,691 A | 8/2000 | Wang et al. | |
| 6,429,224 B1 | 8/2002 | Calabresi et al. | |
| 6,465,427 B1 * | 10/2002 | Blaschuk et al. | 514/9 |
| 6,506,731 B1 * | 1/2003 | Sandberg et al. | 514/15 |

FOREIGN PATENT DOCUMENTS

| EP | 0892084 A2 | 1/1999 |
|---|---|---|
| EP | 969013 A1 | 1/2000 |

OTHER PUBLICATIONS

Wu et'al. Nature 2000, 408(21):1008-12.
Liu et al. Nature 2000, 408(21):1004-07.
Terui et al., Nov. 15, 1999, Cancer Res. 59(22):5651-5.
Magee, Murphy, Mar. 1999, J. Clin, Invest. 103(6):859.
Verhagen et al., Jul. 7, 2000, Cell 102(1):43-53.

* cited by examiner

*Primary Examiner*—Jon Weber
*Assistant Examiner*—Agnes Rooke
(74) *Attorney, Agent, or Firm*—Richard Aron Osman

(57) ABSTRACT

The invention provides methods and compositions for enhancing apoptosis of pathogenic cells. The general method comprises the of contacting the cells with an effective amount of an AV peptoid, wherein the AV peptoid is a peptide comprising $AX_1$, wherein $X_1$ is V, I or L, or a peptide mimetic thereof, which interacts with an Inhibitor of Apoptosis protein (IAP) as measured by IAP binding, pro-caspase-3 activation or promotion of apoptosis, wherein apoptosis of the pathogenic cells is enhanced. The subject compositions encompass pharmaceutical compositions comprising a therapeutically effective amount of a subject AV peptoid in dosage form and a pharmaceutically acceptable carrier, wherein the AV peptoid is a peptide comprising $AX_1$, wherein $X_1$ is V, I or L, or a peptide mimetic thereof, which inhibits the activity of an Inhibitor of Apoptosis protein (IAP) as measured by IAP binding, procaspase-3 activation or promotion of apoptosis. The invention also provides assays for identifying agents which modulates the interaction of an AV peptoid with an IAP, active compounds identified in such screens and their use in the foregoing compositions and therapeutic methods.

14 Claims, No Drawings

US 7,041,784 B2

APOPTOTIC COMPOUNDS

CROSS-REFERENCE TO RELATED APPLICATION

This application is a continuation of and claims priority under 35 U.S.C.§ 120 to Ser. No. 09/645,075, filed Aug. 23, 2000, now U.S. Pat. No. 6,608,026, which is incorporated herein by reference.

This invention was made with Government support under Grant No. GMRO1-57158, awarded by the National Institutes of Health. The Government has certain rights in this invention.

INTRODUCTION

1. Field of the Invention

The field of the invention is promoting cell death.

2. Background

Apoptosis plays a central role in the development and homeostasis of all multi-cellular organisms[1-4]. Abnormal inhibition of apoptosis is a hallmark of cancer and autoimmune diseases, whereas excessive activation of cell death is implicated in neuro-degenerative disorders such as Alzheimer's disease[5,6]. In fact, one mode of action of chemotherapeutic drugs is via the activation of apoptosis; understanding how the cell death program is engaged following an insult, and hence why it fails to be engaged in certain settings, offers a novel approach to overcoming the clinical problem of drug resistance; see, e.g. Makin et al., Cell Tissue Res 2000 July;301(1): 143–52 ("Apoptosis and cancer chemotherapy").

The mechanism of apoptosis is conserved across species and executed with a cascade of sequential activation of initiator and effector caspases[7,8]. Caspases, a family of cysteine proteases with aspartate substrate specificity, are produced in cells as catalytically inactive zymogens[7]. Once activated, the effector caspases are responsible for proteolytic cleavage of a broad spectrum of cellular targets that ultimately lead to cell death.

The Inhibitor of Apoptosis (IAP) family of proteins suppress apoptosis by preventing the activation of procaspases and inhibiting the enzymatic activity of mature caspases[9,10]. Several distinct mammalian IAPs including XIAP, c-IAP1, c-IAP2, and survivin, have been identified, and they all exhibit anti-apoptotic activity in cell culture[9,10]. In Drosopiila, the anti-apoptotic activity of IAPs is removed by Reaper, Grim, and Hid, all of which appear to act upstream of LAPs and physically interact with IAPs to relieve their inhibitory effect on caspase activation[11,12]. IAPs are known to be overexpressed in human cancers[26-33].

One major caspase activation cascade is triggered by the release of cytochrome c from the intermembrane space of mitochondria[13-19]. Concurrent with cytochrome c release, another regulator of apoptosis, Smac[20] (Second mitochondria-derived activator of caspases) or DIABLO[21], is also released from the mitochondria into the cytosol. Smac eliminates the inhibitory effect of multiple IAPs and interacts with all IAPs that have been examined, including XIAP, c-IAP1, c-IAP2, and survivin[20,21].

Smac is synthesized as a precursor molecule of 239 amino acids; the N-terminal 55 residues serve as the mitochondria targeting sequence that is removed after import[20]. The mature form of Smac contains 184 amino acids and behaves as an oligomer in solution[20]. We recently found that the 2.2 Å resolution crystal structure of the mature form of Smac reveals an arch-shaped homo-dimer with rich surface features (the atomic coordinates are being deposited with the Protein Data Bank with the accession number 1FEW). The homo-dimeric interface is dominated by hydrophobic residues through van der Waals interactions. Mutations of key residues at the interface disrupted dimer formation and significantly weakened the ability of Smac to induce the activation of procaspase-3 and to promote the enzymatic activity of mature caspase-3. In addition, similar to the Drosophila proteins Reaper, Grim, and Hid, the N-terminal amino acids of Smac/DIABLO were indispensable for its function; in fact, mutation of the very first amino acid rendered the resulting protein completely inactive. The sequence homology among Reaper, Grim, and Hid is restricted to their N-terminal 14 amino acids; deletion of these residues led to loss of interaction with IAPs[9] and a fusion protein comprising the N-terminal 37-residue peptide of Hid induced apoptosis in insect cells[11]. Here we further disclose small peptides, and peptide mimetics that are sufficient to bind IAP, promote activation of procaspase-3 and/or promote apoptosis.

SUMMARY OF THE INVENTION

The invention provides methods and compositions for enhancing apoptosis of pathogenic cells. The general method comprises the of contacting the cells with an effective amount of an AV peptoid, wherein the AV peptoid is a peptide comprising $AX_1$, wherein $X_1$ is V, I or L, or a peptide mimetic thereof, which interacts with an Inhibitor of Apoptosis protein (IAP) as measured by IAP binding, procaspase-3 activation or promotion of apoptosis, wherein apoptosis of the pathogenic cells is enhanced.

In some embodiments, the cells are in situ in an individual and the contacting step is effected by administering to the individual a pharmaceutical composition comprising a therapeutically effective amount of the AV peptoid, wherein the individual may be subject to concurrent or antecedent radiation or chemotherapy for treatment of a neoproliferative pathology. In other embodiments, the pathogenic cells are of a tumor selected from the group consisting of breast cancer, prostate cancer, lung cancer, pancreatic cancer, gastric cancer, colon cancer, ovarian cancer, renal cancer, hepatoma, melanoma, lymphoma, and sarcoma. In yet other embodiments, the AV peptoid is a peptide comprising $AX_1X_2$, wherein $X_1$ is V, I or L and $X_2$ is P or A; particularly, comprising $AX_1X_2$, wherein $X_1$ is V and $X_2$ is P.

The subject compositions encompass pharmaceutical compositions comprising a therapeutically effective amount of an AV peptoid in dosage form and a pharmaceutically acceptable carrier, wherein the AV peptoid is a peptide comprising $AX_1$, wherein $X_1$ is V, I or L, or a peptide mimetic thereof, which inhibits the activity of an Inhibitor of Apoptosis protein (IAP) as measured by IAP binding, procaspase-3 activation or promotion of apoptosis.

In some embodiments, such compositions further comprise an additional therapeutic agent, such as an anti-neoproliferative chemotherapeutic agent, other than the AV peptoid. In other embodiments of such compositions, the AV peptoid is a peptide comprising $AX_1X_2$, wherein $X_1$ is V, I or L and $X_2$ is P or A; particularly, comprising $AX_1X_2$, wherein $X_1$ is V and $X_2$ is P.

The invention also provides assays for identifying agents which modulates the interaction of an AV peptoid with an IAP, active compounds identified in such screens and their use in the foregoing compositions and therapeutic methods. The general assay comprises the steps of incubating a mixture comprising a subject AV peptoid, a second baculoviral IAP repeat domain (BIR2) of XIAP, and a candidate agent; under conditions whereby, but for the presence of said agent, the peptoid specifically interacts with the BIR2 at a reference affinity; detecting a specific interaction of the peptoid with the BIR2 to determine an agent-biased affinity, wherein a difference between the agent-biased affinity and the reference affinity indicates that the agent modulates the interaction of the peptoid to the BIR2 of the XIAP.

In some embodiments of the screen, the detecting step comprises measuring in vitro binding of the peptoid to the BIR2 by pull-down assay, fluorescent polarization assay or solid-phase binding assay. In other embodiments, the mixture further comprises procaspase-3 and a caspase-3 substrate and the detecting step comprises measuring the interaction inferentially by detecting a reaction product of the caspase-3 substrate and caspase-3 generated by activation of the procaspase-3. In yet other embodiments, the incubating step comprises incubating a cell comprising the mixture and the detecting step comprises measuring the interaction inferentially by detecting apoptosis of the cell, particularly wherein the cell is in situ in an animal host.

DETAILED DESCRIPTION OF PARTICULAR EMBODIMENTS OF THE INVENTION

The following descriptions of particular embodiments and examples are offered by way of illustration and not by way of limitation. Unless contraindicated or noted otherwise in these descriptions and throughout this specification, the terms "a" and "an" mean one or more, the term "or" means and/or and polynucleotide sequences are understood to encompass opposite strands as well as alternative backbones described herein.

An AV peptoid is a peptide comprising $AX_1$, wherein $X_1$ is V, I or L, or a peptide mimetic thereof, which interacts with an Inhibitor of Apoptosis protein (IAP) as measured by IAP binding, procaspase-3 activation or promotion of apoptosis as described in the exemplified activity assays below. In a more particular embodiment, the peptide comprises $AX_1X_2$, wherein $X_1$ is V, I or L preferably V and $X_2$ is P or A, preferably P. The subject AV peptoids are fewer than 20 residues (monomers), preferably fewer than 10, more preferably fewer than 5 and preferably 2 or 3 in length, with a molecular weight of less than about 1,000, preferably less than about 500.

AV peptoids include peptide mimetics of the subject peptides. A peptide mimetic is a non-naturally occurring analog of a peptide which, because of protective groups at one or both ends of the mimetic, or replacement of one or more peptide bonds with non-peptide bonds, is less susceptible to proteolytic cleavage than the peptide itself. For instance, one or more peptide bonds can be replaced with an alternative type of covalent bond (e.g., a carbon-carbon bond or an acyl bond). Peptide mimetics can also incorporate amino-terminal or carboxyl terminal blocking groups such as t-butyloxycarbonyl, acetyl, alkyl, succinyl. methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl, thereby rendering the mimetic less susceptible to proteolysis. Non-peptide bonds and carboxyl- or amino-terminal blocking groups can be used singly or in combination to render the mimetic less susceptible to proteolysis than the corresponding peptide. Additionally, substitution of D-amino acids for the normal L-stereoisomer can be effected, e.g. to increase the half-life of the molecule. Accordingly, the peptide mimetics include peptides having one or more of the following modifications:

peptides wherein one or more of the peptidyl [—C(O) NR—] linkages (bonds) have been replaced by a non-peptidyl linkage such as a —$CH_2$-carbamate linkage [—$CH_2$—OC(O)NR—]; a phosphonate linkage; a —$CH_2$-sulfonamide [—$CH_2$—S(O)$_2$NR—] linkage; a urea [—NHC(O)NH—] linkage; a —$CH_2$-secondary amine linkage; or an alkylated peptidyl linkage [—C(O)NR$^6$— where R$^6$ is lower alkyl];

peptides wherein the N-terminus is derivatized to a —NRR$^1$ group; to a —NRC(O)R group; to a —NRC(O)OR group; to a —NRS(O)$_2$R group; to a —NHC(O)NHR group, where R and R$^1$ are hydrogen or lower alkyl with the proviso that R and R$^1$ are not both hydrogen: to a succinimide group; to a benzyloxycarbonyl-NH—(CBZ-NH—) group; or to a benzyloxycarbonyl-NE— group having from 1 to 3 substituents on the phenyl ring selected from the group consisting of lower alkyl, lower alkoxy, chloro, and bromo; or peptides wherein the C terminus is derivatized to —C(O)R$^2$ where R$^2$ is selected from the group consisting of lower alkoxy, and —NR$^3$R$^4$ where R$^3$ and R$^4$ are independently selected from the group consisting of hydrogen and lower alkyl.

Preferred mimetics have from zero to all of the —C(O) NH— linkages of the peptide replaced by a linkage selected from the group consisting of a —CR$_2$OC(O)NR— linkage; a phosphonate linkage; a —$CH_2$S(O)$_2$NR— linkage; a —$CH_2$NR— linkage; and a —C(O)NR$^6$— linkage, and a —NHC(O)NH— linkage where R is hydrogen or lower alkyl and R$^6$ is lower alkyl, and wherein the N-terminus of the mimetic is selected from the group consisting of a —NRR$^1$ group; a —NRC(O)R group; a —NRC(O)OR group; a —NRS(O)$_2$R group; a —NHC(O)NHR group; a succinimide group; a benzyloxycarbonyl-NH— group; and a benzyloxycarbonyl-NH— group having from 1 to 3 substituents on the phenyl ring selected from the group consisting of lower alkyl, lower alkoxy, chloro, and bromo, where R and R$^1$ are independently selected from the group consisting of hydrogen and lower alkyl, and still further wherein the C-terminus of the mimetic has the formula —C(O)R$^2$ where R$^2$ is selected from the group consisting of hydroxy, lower alkoxy, and —NR$^3$R$^4$ where R$^3$ and R$^4$ are independently selected from the group consisting of hydrogen and lower alkyl and where the nitrogen atom of the —NR$^3$R$^4$ group can optionally be the amine group of the N-terminus of the peptide so as to form a cyclic peptide, and physiologically acceptable salts thereof.

An important aspect of the invention is drawn to peptoids comprising N-substituted glycine analogs which resemble naturally-occurring amino acids (i.e., Ala, Cys, Asp, Glu, Phe, Gly, His, Ile, Lys, Leu, Met, Asn, Pro, Gln, Arg, Ser, Thr, Val, Trp, and Tyr) and comprising the general formula I: $X_n NRCH_2COOX_c$, wherein the radicals $X_n$ and $X_c$ are either chains of conventional amino acids, chains of one or more N-substituted glycine analogs, or chains in which conventional amino acids and N-substituted glycine analogs are interspersed.

Preferred N-substituted glycine analogs are those in which R is ethyl, prop-1-yl, prop-2-yl, 1-methylprop-1-yl, 2-methylprop-1-yl, benzyl, 4-hydroxybenzyl, 2-hydroxyethyl, mercaptoethyl, 2-aminoethyl, 3-aminopropyl, 4-aminobutyl, 2-methylthioeth-1-yl, carboxymethyl, 2-carboxyethyl, carbamylmethyl, 2-carbamylethyl, 3-guanidinoprop- 1-yl, imidazolylmethyl, or indol-3-yl-ethyl, particularly where R is 2-methylpropyl, benzyl, 2-hydroxyethyl, 2-aminoethyl, or carboxymethyl. The resemblance between amino acid and substitute need not be exact. For example, one may replace lysine with compounds of formula I in which R is aminomethyl, 2-aminoethyl, 3-aminopropyl, 4-aminobutyl, 5-aminopentyl, or 6-aminohexyl. Serine may be replaced with hydroxymethyl, 2-hydroxyethyl, 3-hydroxypropyl, 2-hydroxypropyl, and the like. In general, a conventional amino acid may be replaced with an N-substituted glycine analog having a sidechain of similar character, e.g, hydrophobic, hydrophilic, polar, nonpolar, aromatic, etc.

Monomer refers to a molecule which may be linked to other monomers to form a peptoid. Monomers include amino acid substitutes, which may include N- and/or C-terminal modifications to facilitate linking, for example, leaving or activating groups.

N-substituted glycine analog refers to compounds of the formula RNH—CH$_2$—COOH, where R is as defined above. The salts and esters of these compounds, as well as compounds of the formula,bearing standard protecting groups (e.g., Fmoc, t-Boc, and the like) are also considered within the definition of "monomer" and "N-substituted glycine analog" unless otherwise specified.

A peptoid of the invention corresponds to a natural peptide if it elicits a biological activity related to the biological activity of the natural protein. The elicited activity may be the same as, greater than or less than that of the natural protein, i.e., provide enhanced and/or blocking effects. In general, such a peptoid will have an essentially corresponding monomer sequence, where a natural amino acid is replaced by an N-substituted glycine derivative, if the N-substituted glycine derivative resembles the original amino acid in hydrophilicity, hydrophobicity, polarity, etc. Thus, the following pairs of peptoids would be considered corresponding in monomer sequence:

Ia:
Ala-Val-Ile

Ib:
Ala-Val*-Ile*

IIa:
Ala-Ile-Pro-Gly-Phe-Ser-Pro-Phe        (SEQ ID NO:1)

IIb:
Ala-Ile-Pro-Gly-Phe*-Ser*-Pro-Phe*     (SEQ ID NO:2)

IIIa:
Ala-Leu-Phe-Met-Thr                    (SEQ ID NO:3)

IIIb:
Ala-Leu-Phe*-Met-Ser*                  (SEQ ID NO:4)

In these examples, "Val*" refers to N-(prop-2-yl)glycine, "Phe*" refers to N-benzylglycine. "Ser*" refers to N-(2-hydroxyethyl)glycine, "Leu*" refers to N-(2-methylprop-1-yl)glycine, and "Ee*" refers to N-(1-methylprop-1-yl)glycine.

The correspondence need not be exact: for example, N-(2-hydroxyethyl)glycine may substitute for Ser, Thr, Cys, and Met;. N-(2-methylprop-1-yl)glycine may substitute for Val, Leu, and Ile. Note in IIIa and IIIb above that Ser* is used to substitute for Thr and Ser despite the structural differences: the sidechain in Ser* is one methylene group longer than that of Ser, and differs from Thr in the site of hydroxy-substitution. In general, one may use an N-hydroxyalkyl-substituted glycine to substitute for any polar amino acid, an N-benzyl- or N-aralkyl-substituted glycine to replace any aromatic amino acid (e.g., Phe, Trp, etc.), an N-alkyl-substituted glycine such as N-butylglycine to replace any nonpolar amino acid (e.g., Leu, Val, Ile, etc.), and an N-(aminoalkyl)glycine derivative to replace any basic polar amino acid (e.g., Lys and Arg).

The peptoids of the invention can be produced using amino acids as the monomer units or amino acid substitutes. Examples of different modifications in amino acids which can be carried out in order to obtain the amino acid substitutes used in the invention are put forth below in Table 1.

TABLE 1

Peptoid Modification Chemistry

| Type of Modification | | Isosteric | Enzyme Resistance | H-Bonding | Chiral Monomer |
|---|---|---|---|---|---|
| I | Peptoids | | | | |
| II | N-alkylation | + | +++ | + | Yes |
| III | α-Ester | +++ | + | +++ | Yes |
| IV | Thioamide | +++ | ++ | + | Yes |
| V | N-hydroxylation | + | +++ | + | Yes |
| VI | β-Ester | + | ++ | ++ | Yes |
| VII | Sulfonamide | + | ++ | ++ | No |
| VIII | Sulfonamide-N | + | ++ | ++ | No |
| IX | Urea | + | ++ | ++ | No |
| X | Urethane | + | ++ | ++ | No |

Items II, III, IV and IX are taken from Spatola, A., "Peptide Backbone Modifications: . . . " in Chemistry and Biochemistry of Amino Acids, Peptides, and Proteins (1983) 7:267, B. Weinstein ed.. The + refers to the extent to which replacement is characterized by the given property: + = minimal, ++ = partial, +++ = substantial.

As can be seen from the table, modifications can significantly alter the properties of the molecules, particularly with respect to enzymatic hydrolysis. From a synthetic-standpoint., chiral starting materials can be problematic. Even if they are easily synthesized, the fidelity of the subsequent coupling reactions needs to be addressed. Each substitute amino acid structure is discussed briefly below and can be compared to the amino acid structure in a peptide.

I. Peptide. The individual monomer units or substitute peptides such as those described below can be combined together in any manner. However, it is most preferable to combine the monomer units using methodology such as disclosed in WO89/10931 in order to obtain large libraries of different peptoids, which libraries can then be screened to find one or more peptoids which has a particular characteristic such as a high affinity for a particular receptor site. Although the substitute amino acids put forth below are examples of preferred substitute amino acids which can be used in connection with producing peptoids of the invention, it should be noted that any monomer unit can be used which would allow for sequence specific synthesis of pools of diverse molecules. Any such monomer unit would be suitable for use in connection with the present invention in that such units would make it possible to search and screen for particular conformational shapes which have affinity for particular receptor sites. The use of nonpeptide polymers is believed to have particular advantages over conventional peptides in that such peptoids would occupy different conformational configurations in space and should provide resistance to the action of proteases, which feature would be particularly important to designing conjugates wherein the peptoid portion would have a desirably long half-life. Further, substitute amino acids could be designed so as to provide for molecules which are generally easier to synthesize than conventional peptides might be.

II. N-alkylated glycines. The main advantages of this system are the ease of synthesis of the properly protected achiral monomers and the vast literature of peptides concerning the synthesis and characterization of the closely related peptoid polymers. The main disadvantage is the decrease in properties dependent on the availability of amide protons for hydrogen bonding, such as solubility in aqueous systems, conformational rigidity, secondary structure, etc. It is pointed out that N-alkylated glycines are a preferred class of N-substituted glycines which can be used in connection with the present invention. Thus other chemically compatible groups other than R=alkyl may be used. Further, the substitutions may be made on the nineteen other natural amino acids.

III. α-Esters. Polyesters are one of the closest relatives to the normal peptide bonds. The advantage is the close similarity, however, this can also be a drawback since proteolytic enzymes are known to recognize esters or even prefer esters as their substrates. α.-Polyesters are prepared from chiral .alpha.-hydroxy acids in which there has been considerable synthetic interest (Chan, P. C., et al., Tetrahedron Lett (1990) 31:1985). In a stepwise fashion, polymers can be assembled much as polyamides are prepared.

IV. Thioamides. The thioamide is also rather similar to the normal peptide. According to Clausen, K., et al., J Chem Soc Perkin Trans (1984) 1:785, until 1984 there had been only limited reports of the thioamide replacement for a peptide bond which they attribute to the difficulty in synthesis. He describes the synthesis and use of a protected thioamide precursor using Lawessons's reagent. Also, a recent report (Tetrahedron Lett (1990) 31:23) describes the conversion of a peptide bond to a thioamide using the same reagent.

V. N-hydroxy amino acids. The advantages are the decreased sensitivity to enzyme hydrolysis and H-bonding ability due to the added hydroxyl group. Kolasa et al. has described the synthesis of N-hydroxypeptides (Kolasa, T., et al, Tetrahedron (1977) 33:3285).

VI. β-Ester. This is an example of a homologue of the .alpha.-ester. Presumably the different spacing will confer some special properties such as increased resistance to enzyme hydrolysis or novel conformational flexibility. The appropriate starting materials are readily synthesized (Elliott, J., et al., Tetrahedron Lett (1985) 26:2535, and Tetrahedron Lett (1974) 15:1333.

VII. and VIII. Sulfonamides. The two sulfonamides differ by the positioning of the R group. According to Frankel and Moses (Frankel, M., et al., Tetrahedron (1960) 9:289), the peptide analog, i.e., the 1,4 substituted polymer is not stable under their condensation conditions. Compounds of the type VII are readily obtained from chiral β-amino alcohols (Kokotos, G., Synthesis (1990) 299) while those of the type VIII are achiral and easily synthesized.

IX. Ureas. Ureas are also conveniently synthesized from carboxylic acids and amines using the reagent diphenylphosphoryl azide, DPPA (Shiori, T., et al., J Am Chem Soc (1972) 94:6203, and Bartlett, P., et al., Synthesis (1989) 542). Previously prepared peptoids with a single urea replacement had properties similar to the starting peptide (see reference 1, p. 231). Additionally, since there is still an amide proton available for H-bonding, the solubility properties may be better than for N-alkylated glycines.

X. Urethanes. The structure of a urethane is slightly different than that of a urea and would presumably have altered properties. Aqueous solubility may be somewhat reduced since the amide-proton is removed. The polymers may be prepared via simple chemistry.

There are numerous other polymer systems which could be employed for the purpose of searching conformational space. Most notable are the phosphorous derived polymers with phosphonamides as one example (Yamauchi, K., et al., Bull Chem Soc Japan (1972) 45:2528). Polyamines (Tetrahedron Lett (1990) 31:23, and Kaltenbronn, J. S., et al., in Proceedings of the Eleventh American Peptide Symposium (1989) 969, J. Rivier, ed.), polyalkanes, polyketones (Almquist, G., et al., J Med Chem (1984) 27:115, polythioethers. polysulfoxides (Spatola, A., et al., Biopolymers (1986) 25:S229) and polyethers may be less suitable for our purposes due to either difficulty in synthesis or predictably poor properties (e.g., polyamines would carry a positive charge at every junction and require double amine protection during synthesis). In summary, several alternatives to N-alkylated glycine polymers of which libraries could be constructed have been described.

The foregoing examples of mimetics are nonlimiting. Peptide mimetic chemistry is a well-established art wherein skilled practitioners can readily generate a wide variety of mimics using conventional chemistry (see, e.g. Liao et al. (1998) J.Med.Chem 41, 4767–4776; Andrade-Gordon et al. (1999) PNAS USA 96, 12257–12262; Boatman et al. (1999) J. Med. Chem. 42, 1367–1375; Kasher et al. (1999) J.Mol-.Biol 292,421–429; U.S. Pat. No. 5,981,467; etc.) and these other strategies are applicable here, so long as the resultant mimetics are screened for and demonstrated to provide the requisite IAP inhibitory activity as assayed below.

Synthetic methods for producing the subject peptoids are well-known in the art. Some general means for the production of peptides, analogs or derivatives are outlined in *Chemistry and Biochemistry of Amino Acids, Peptides and Proteins, A Survey of Recent Developments*, Weinstein, B. ed., Marcell Dekker, Inc., publ. New York (1983). A wide variety of well-established techniques are available for synthesizing peptide mimetics, see. e.g. submonomer method of R. Zuckermann et al., J. Am. Chem. Soc. (1992) 0114: 10646–7. Synthesis by solid phase techniques of heterocyclic organic compounds in which N-substituted glycine monomer units forms a backbone is described in U.S. Pat. No. 5,958,792. wherein combinatorial libraries of mixtures of such heterocyclic organic compounds can then be assayed for the ability to inhibit IAP as described below. Highly substituted cyclic structures can be synthesized on a solid support by combining the submonomer method with powerful solution phase chemistry. Cyclic compounds containing one, two, three or more fused rings are formed by the submonomer method by first synthesizing a linear backbone followed by subsequent intramolecular or intermolecular cyclization, also as described in U.S. Pat. No. 5,958,792. General preparative protocols for exemplary peptoid classes are as follows:

Preparation of α-Polyesters Using Chiral α-Hydroxy Acids As Building Blocks. The α-polyester structures can be prepared by using chemical synthesis technology known to those skilled in the art. For details of the reaction, see Brewster, P., et al., Nature, ( 1990) 166:179. An alternative method for producing similar structures is disclosed in Chan, P. C., and Chong, J. M., Tetrahedron Lett. (1990)1985. Further, various publications cited within the Chan et al. publication describe techniques for synthesizing chiral α-hydroxy acids.

Preparation of Polythioamides Using Chiral .alpha.-Amino Acids As Building Blocks. Polythioamide structures can be synthesized using techniques such as those described in Clausen, K., et al., J. Chem. Soc. Perkin Trans. 1 (1984) 785, and Tetrahedron Lett. (1990) 31:23.

Preparation of Polyhydroxymates Using Chiral .alpha.-Amino Acids As Building Blocks. Polyhydroxymates can be synthesized using techniques as disclosed in Kolasa. T. and Chimiak, A., Tetrahedron (1977) 33:3285. References cited within Kolasa disclose and describe chemical techniques for synthesizing N-hydroxy amino acids which can be used in peptoid synthesis.

Preparation of β-Polyesters Using Chiral 13-Hydroxy Acids As Building Blocks. β-polyesters can ₁be synthesized using a synthesis protocol as described in Elliott, J. D. et al. Tetrahedron Lett. (1985) 26:2535, and Tetrahedron Lett. (1974) 15:1333.

Preparation of Polysulfonamides Using Chiral β-Amino Sulfonic Acids As Building Blocks. Polysulfonamides can be synthesized using the reaction scheme shown in U.S. Pat. No. 6,075,121. The chiral β-amino acids have been described within Kokotos, G., Synthesis (1990) 299.

Preparation of N-alkylated Polysulfonamides Using Achiral β-Amino Sulfonic Acids As Building Blocks. Similarly, these polysulfonamides can be synthesized using the reaction scheme shown in U.S. Pat. No.6,075,121.

Preparation of Polyureas Using Achiral β-amino Acids As Building Blocks. Polyureas can be synthesized using techniques such as those described in Shiori, T., et al., J. Am. Chem. Soc. (1972) 94:6302, and Scholtz, J., and Bartlett, P., Synthesis (1989) 542.

Preparation of Polyurethanes Using Achiral β-Amino Alcohols As Building Blocks. Polyurethanes can be synthesized using the reaction scheme shown in U.S. Pat. No. 6,075,121. Individual N-substituted glycine analogs are known in the art, and may be prepared by known methods. See, for example, Sempuku et al., JP 58/150,562 (Chem Abs (1984) 100:68019b); Richard et al., U.S. Pat. No. 4,684,483; and Pulwer et al., EPO 187,130.

Several N-substituted glycine derivatives are available from commercial sources. For example, N-benzylglycine is available from Aldrich Chemical Co. (Milwaukee, Wis.) as the ethyl ester. The ester is hydrolyzed in KOH/MeOH, then protonated in HCl to yield N-benzylglycine. This may then be protected with Fmoc (fluorenylmethoxycarbonyl) by treatment with Fmoc-Cl in aqueous dioxane at high pH (about 10).

Other N-substituted glycine analogs are synthesized by simple chemical procedures. N-isobutylglycine may be prepared by reacting excess 2-methylpropylamine with a halo-acetic acid.

N-(2-aminoethyl)glycine may be prepared by reacting excess 1,2-diaminoethane with a haloacetic acid and purifying on Dowex-1® (OH form), eluting with acetic acid. The unprotected amine is protected with t-butoxycarbonyl (t-Boc) using conventional techniques at pH 11.2, followed by protection of the secondary amine with Fmoc.

N-(2-hydroxyethyl)glycine may be prepared by reacting excess 2-aminoethanol with haloacetic acid and purifying on Dowex-1® (OH form), eluting with acetic acid. The amine nitrogen is then protected with Fmoc. Next, the acid group is esterified with methanol under acidic conditions. The methyl ester is then treated with isobutylene to form the t-butyl ether. Then, the methyl ester is hydrolyzed using porcine liver esterase in phosphate buffer at pH 8.0, to provide a protected N-substituted glycine analog in a form suitable for peptoid synthesis. As an alternative to the above, the Fmoc-hydroxyethylglycine is treated with t-butyldiphenylsilylchloride in DMF and imidazole to give a silyl-protected alcohol.

N-(carboxymethyl)glycine may be prepared by reacting glycine t-butyl ester with 2-haloacetate in aqueous solution. The product may be protected directly by addition of Fmoc. As an alternative, the N-(carboxymethyl) glycine may be prepared by mixing glycine t-butyl ester, glyoxylic acid and palladium on charcoal under an atmosphere of hydrogen in water at pH 6. The compound is then treated with FMOC in the usual manner.

Once the monomers have been synthesized, they may be coupled with other monomers and/or conventional amino acids to form analogs using standard peptide chemistry. For example, an Fmoc-protected monomer (N-substituted glycine or conventional amino acid) may be immobilized on a suitable resin (e.g., HMP) by reaction with benzotriazol-1-yloxy-tris(dimethylamino)phosphonium hexafluorophosphate (BOP) or a carbodimide (for example, dicyclohexyl-carbodiimide) under basic conditions (e.g., pH 9) in a suitable solvent. The Fmoc protecting group is removed by treatment with piperidine. Each additional monomer is then attached sequentially using BOP or a carbodiimide, until the entire sequence has been constructed. The completed chain is then detached from the resin and the sidechain deprotected by treating with trifluoroacetic acid (TFA).

Alternatively, one may connect N-substituted glycine analogs to the ends of peptoids produced by other methods, for example, by recombinant expression or isolation from natural sources. Further, N-substituted glycine analogs may be inserted within the sequence of such peptoids by cleaving the peptoid at the desired position, attaching an N-substituted glycine analog, and reattaching the remainder of the molecule or a chemically-synthesized replacement.

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the peptoid is usually a minor component (from about 0.1 to about 50% by weight or preferably from about 1 to about 40% by weight) with the remainder being various vehicles or carriers and processing aids helpful for forming the desired dosing forn.

Suitable excipients or carriers and methods for preparing administrable compositions are known or apparent to those skilled in the art and are described in more detail in such publications as *Remington's Pharmaceutical Science*, Mack Publishing Co, NJ (1991). In addition, the peptoids may be advantageously used in conjunction with other chemotherapuetic agents such as diethylstilbestrol or DES, 5-fluorouracil, methotrexate, interferon-alpha, aspariginase, tamoxifen, flutamide, etc, and chemotherapeutic agents described in the *Merck Manuel*, 16th edition 1992, Merck Research Laboratories, Rahway, N.J.; *Goodman & Gilman's The Pharmacological Basis of Therapeutics*, $9^{th}$Ed., 1996, McGraw-Hill, esp. Chabner et al., *Antineoplastic Agents* at pp. 1233, etc. or otherwise known in the art. Hence the agents and peptoids may be administered separately, jointly, or combined in a single dosage unit. In a particular embodiment, the combination therapy is effected by a conjugate of the peptoid bound covalently to the anti-neoproliferative chemotherapeutic or other pharmaceutically active agent. Any suitable conjugation chemistry may be used, such as derivatizing the N-terminus of the peptoids and conjugating the drug through an amid linkage.

The amount administered depends on the AV peptoid formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 0.1 mg to 1000 mg, preferably from about 1 mg to 300 mg, more preferably 10 mg to 200 mg, according to the particular application. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The following are examples (Examples 1–4) of capsule formulations for the peptoids of Table 2.

TABLE 2

Capsule Formulations

| Capsule Formulation | Formula 1 mg/capsule | Formula 2 mg/capsule | Formula 3 mg/capsule | Formula 4 mg/capsule |
|---|---|---|---|---|
| Solid Solution | 100 | 400 | 400 | 200 |
| Silicon Dioxide | 0.625 | 2.5 | 3.75 | 1.875 |
| Magnesium Stearate NF2 | 0.125 | 0.5 | 0.125 | 0.625 |
| Croscarmellose Sodium NF | 11.000 | 44.0 | 40.0 | 20.0 |
| Pluronic F68 NF | 6.250 | 25.0 | 50.0 | 25.0 |
| Silicon Dioxide NF | 0.625 | 2.5 | 3.75 | 1.875 |
| Magnesium Stearate NF | 0.125 | 0.5 | 1.25 | 0.625 |
| Total | 118.750 | 475.00 | 475.00 | 475.00 |
| Capsule Size | No. 4 | No. 0 | No. 0 | No. 2 |

Preparation of Solid Solution

Crystalline peptoid (80 g/batch) and the povidone (NF K29/32 at 160 g/batch) are dissolved in methylene chloride (5000 mL). The solution is dried using a suitable solvent spray dryer and the residue reduced to fine particles by grinding. The powder is then passed through a 30 mesh screen and confirmed to be amorphous by x-ray analysis.

The solid solution, silicon dioxide and magnesium stearate are mixed in a suitable mixer for 10 minutes. The mixture is compacted using a suitable roller compactor and milled using a suitable mill fitted with 30 mesh screen. Croscarmellose sodium, Pluronic F68 and silicon dioxide are added to the milled mixture and mixed further for 10 minutes. A premix is made with magnesium stearate and equal portions of the mixture. The premix is added to the remainder of the mixture, mixed for 5 minutes and the mixture encapsulated in hard shell gelatin capsule shells.

AV peptoids can be administered by a variety of methods including, but not limited to, parenteral, topical, oral, or local administration, such as by aerosol or transdermally, for prophylactic and/or therapeutic treatment. The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

The particular choice of peptoid, chemotherapeutic agent and/or radiation depends upon the diagnosis of the attending physicians and their judgement of the condition of the patient and the appropriate treatment protocol. The peptoid, chemotherapeutic agent and/or radiation may be administered concurrently (e.g., simultaneously, essentially simultaneously or within the same treatment protocol) or sequentially, in any order, depending upon the nature of the proliferative disease, the condition of the patient, and the actual choice of chemotherapeutic agent and/or radiation to be administered in conjunction (i.e., within a single treatment protocol) with the peptoid. Similarly, the peptoid and the chemotherapeutic agent do not have to be administered in the same pharmaceutical composition, and may, because of different physical and chemical characteristics, be administered by different routes.

In one embodiment of the present invention, the method of the invention includes systemic or local administration of an AV peptoid. Where systemic administration is desired the peptoid may be administered, for example, by intravenous injection or orally. One embodiment of the invention provides local administration of the peptoid, for example, at the tumor site. With local administration of the peptoid, the preferred mode of administration is by local injection. However, local administration may also be by catheter, or by local deposition, for example by intra- or peritumoral administration of products sold under the trademark Depofoam®, slow release pump/drug delivery service, implantable or topical gel or polymer, depending on the nature and location of the tumor. Administration of the therapeutics of the invention can also be effectd by gene therapy protocol.

The therapeutics of the invention can be administered in a therapeutically effective dosage and amount, in the process of a therapeutically effective protocol for treatment of the patient. The initial and any subsequent dosages administered will depend upon the patient's age, weight, condition, and the disease, disorder or biological condition being treated. Depending on the therapeutic, the dosage and protocol for administration will vary, and the dosage will also depend on the method of administration selected, for example, local or systemic administration. For a very potent peptoid, microgram (ug) amounts per kilogram of patient may be sufficient, for example, in the range of about 1 ug/kg to about 500 mg/kg of patient weight, and about 100 ug/kg to about 5 mg/kg, and about 1 ug/kg to about 50 ug/kg, and, for example, about 10 ug/kg.

In general, routine experimentation in clinical trials will determine specific ranges for optimal therapeutic effect, for each therapeutic, each administrative protocol, and administration to specific patients will also be adjusted to within effective and safe ranges depending on the patient condition and responsiveness to initial administrations. However, the ultimate administration protocol will be regulated according to the judgment of the attending clinician considering such factors as age, condition and size of the patient as well as peptoid potency, severity of the disease being treated. For example, a dosage regimen of the peptoids can be oral administration of from 10 mg to 2000 mg/day, preferably 10 to 1000 mg/day, more preferably 50 to 600 mg/day, in two to four (preferably two) divided doses to reduce tumor growth. In a preferred embodiment, in cases where the peptoid is based on a fused-ring cyclic benzocycloheptapyridine, the preferred dosage of the inhibitor is oral administration of from 50 to 600 mg/day, more preferably 50 to 400 mg/day, in two divided doses. Intermittant therapy (e.g., one week out of three weeks or three out of four weeks) may also be used.

In one example of combination therapy in the treatment of pancreatic cancer, the peptoid is selected from Table 4 or 5, administered orally in a range of from 50 to 400 mg/day, in two divided doses, on a continuous dosing regimen; and the antineoplastic agent is gemcitabine administered at a dosage of from 750 to 1350 mg/m$^2$ weekly for three out of four weeks during the course of treatment. In another example of combination therapy in the treatment of lung cancer, the peptoid is selected from Table 4 or 5, administered orally in a range of from 50 to 400 mg/day, in two divided doses, on a continuous dosing regimen; and the antineoplastic agent is paclitaxel administered at a dosage of from 65 to 175 mg/M$^2$ once every three weeks. In another example of combination therapy in the treatment of gliomas the peptoid is selected from Table 1, administered orally in a range of from 50 to 400 mg/day, in two divided doses; and the antineoplastic agent is temozolomide administered at a dosage of from 100 to 250 mg/m$^2$. In another example of combination therapy, the peptoid is selected from Table 4 or 5, administered orally in a range of from 50 to 400 mg/day, in two divided doses, on a continuous dosing regimen; and the antineoplastic agent is 5-Fluorouracil (5-FU) administered either at a dosage of 500 mg/m$^2$ per week (once a week), or at a dosage of 200–300 mg/m$^2$ per day in the case of continuous infusion of the 5-FU. In the case of 5-FU administration on a weekly injection, 5-FU may be administered in combination with a foliate agonist, e.g., Leucovoran (at a dosage of 20 mg/m$^2$/week).

A preferred embodiment of the invention includes monitoring the effects of the treatment with an AV peptoid for signs of tumor regression, and subsequently adjusting the administration,of further doses accordingly. For example, a person with breast carcinoma would be treated locally with an agent such as cyclophosphamide methotrexate 5-FU (CM F) or tamoxifen or local radiation therapy and an AV peptoid. Subsequent mammography, ultrasound, or physical exams, as compared with the same pre-treatment tests, would direct the course and dosage of further treatment.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, and successive measurements can be used to judge whether or not growth of the tumor has been retarded or even reversed. Relief of disease-related symptoms such as pain, and improvement in overall condition can also be used to help judge effectiveness of treatment. Accordingly, preferred embodiments of the invention include monitoring of the patient after treatment with an AV peptoid for signs of tumor regression. Such monitoring includes but is not limited to physical exam, CT scan, MRI. mammography, chest X-rays, bone scans, ultrasounds, bronchoscopy, endoscopy, colonoscopy, laparoscopy, and tests for tumor markers such as PSA, CEA, and CA125. The appropriateness of any form of monitoring will be determined by the nature of the cancer being treated.

EXAMPLES

Preparation of Monomers. Representative monomers of the invention, suitable for peptoid construction, were prepared as set forth below. Efforts have been made throughout the examples to insure accuracy with respect to numbers used (e.g., amounts, temperature, pH, etc.) but some experimental errors and deviation should be accounted for. Unless indicated otherwise, parts are parts by weight, temperature is in degrees centigrade, and pressure is at or near atmospheric.

Example 1

FMOC—N-Benzylglycine

A. Reaction 1

N-benzylglycine ethyl ester (Aldrich, 4.0 mL, 20.9 mmol) was dissolved in methanol (40 mL) and treated overnight with aqueous KOH (10 M, 8 mL) at room temperature. TLC indicated complete conversion to product. The solution was cooled in an ice bath and carefully acidified to pH 2 with HCl. White crystals were collected and recrystallized from aqueous methanol, to provide 3.95 g (93%) of the HCl salt.

B. Reaction 2

N-benzylglycine.HCl (1.07 g, 5.3 mmol) was dissolved in aqueous acetonitrile, and the pH brought to 9–10 with 1 N NaOH. A solution of FMOC—Cl in acetonitrile was added dropwise, and the pH maintained by adding base, until the reaction was complete (as judged by TLC). The pH of the solution was lowered to 4, and the solution extracted with ethyl acetate. The organic layer was washed with water and dried over sodium sulfate. Silica gel chromatography (ethyl acetate/hexanes) yielded FMOC—N-benzylglycine as an oil (1.43 g. 70%), which could be recrystallized from acetic acid/methanol. This monomer may be used in peptoids at any position at which an aromatic side chain is desired.

Example 2

FMOC—N-isobutylglycine

A. Reaction 3

Isobutylamine (50 mL, 0.5 mol) was cooled in an ice bath, and bromoacetic acid (6.1 g, 43.9 mmol) added slowly as a solid, insuring that each piece dissolved. After stirring overnight, the excess amine was removed and MeOH was added to the resulting oil. The resulting mixture was concentrated, and repeated using MeOH/HCl. Finally, a white solid was recrystallized from ethanol/ether to provide N-isobutylglycine.HCl (3.95 g, 53.7%).

B. Reaction 4

N-isobutylglycine.HCl (1.25 g, 7.46 mmol) was dissolved in aqueous acetonitrile and treated with FMOC—Cl as described in part (A) above. After the reaction was complete, the pH was lowered to 2.5 and the aqueous solution extracted with ethyl acetate. The organic layer was washed with water, saturated NaCl, and dried over sodium sulfate. Silica gel chromatography (ethyl acetate/hexanes) yielded FMOC—N-isobutylglycine as an oil (1.29 g, 47%). Additiohal material could be recovered from impure chromatographic fractions. This monomer may be used in peptoids at any position at which an aliphatic, hydrophobic side chain is desired.

Example 3

FMOC—N—(N'—BOC-2-aminoethyl)glycine

A. Reaction 5

Ethylenediamine (65 mL, 0.97 mol) was cooled in an ice bath, and chloroacetic acid (10.0 g, 0.106 mol) added in small portions, allowing each portion to dissolve. After the addition was complete, the solution was allowed to stir overnight at room temperature. Water was added and the solution applied to a Dowex®-AG-1 column (OH$^-$ form, 2.5×50 cm). The column was washed with water (2 L) until ninhydrin-negative, and the product eluted with 0.5 N HOAc. The ninhydrin-positive fractions were pooled, concentrated, and recrystallized from EtOH/Et$_2$O/HCl to provide N-2-aminoethylglycine.HCl (9.7 g, 48%).

B. Reaction 6

N-2-aminoethylglycine.HCl (2.5 g, 13.1 mmol) was dissolved in water (20 mL) and dioxane (25 mL). The pH was brought to 11.2 with concentrated NaOH. BOC-nitrophenylcarbonate (3.5 g, 14.6 mmol) was dissolved in dioxane (20 mL) and added over 45 min with stirring, maintaining the pH with a pH stat. After the addition, the solution was stirred for one day at constant pH. Water was then added, the pH lowered to 6, and the resulting solution extracted with ether. The pH was further lowered to 3 with KHSO$_4$ and extracted with ether, then lowered to 2 and extracted with EtOAc. TLC indicated that the product remained in the aqueous layer. The product was used without further purification.

The pH of the solution was adjusted to 9.5 with NaOH, providing a total volume of about 200 mL. Acetone (50 mL) was then added, and FMOC—N-hydroxysuccinimide (4.64 g, 13.6 mmol) in acetone (100 mL) added dropwise while maintaining the pH. The reaction mixture was stirred overnight. The basic solution was extracted with ether and carefully acidified to pH 2.5 with HCl and KHSO$_4$. The acidic solution was washed with saturated NaCl and dried over sodium sulfate. After concentration, the solid was recrystallized from ethyl acetate/hexanes to provide FMOC—N—(N'—BOC-2-aminoethyl)glycine (4.74 g, 57% for two steps). This monomer may be used in peptoids at any position at which a basic side chain is desired.

Example 4

FMOC—N-(2-t-butoxyethyl)glycine

A. Reaction 7

Ethanolamine (60 mL) was cooled in an ice bath, and chloroacetic acid (10.0 g, 10.5 mmol) added in portions, allowing each portion to fully dissolve. The solution was then heated to 60° C. for one hour. After cooling, the product was applied to a Dowex®-AG1 column (OH$^-$ form, 2.5×50 cm). The column was washed with water until the washes were ninhydrin-negative, and the product eluted with 0.5 N HOAc. After concentration, N-2(hydroxyethyl) glycine (9.8 g, 52%) was obtained.

B. Reaction 8

N-2(hydroxyethyl) glycine (5.18 g, 28.9 mmol) was dissolved in 1 N NaOH (60 mL) and dioxane (60 mL). The pH was adjusted to 9.5 and the solution cooled in an ice bath. FMOC—Cl (10.0 g, 38.7 mmol) in dioxane (50 mL) was added dropwise with stirring while maintaining the pH by addition of NaOH. After the addition was complete, the solution was allowed to stir at room temperature for two more hours. The basic solution was extracted with ether. Then, the solution was carefully acidified to pH 2.5 with HCl, and the acidic solution extracted with EtOAc, which was washed with NaCl and dried over sodium sulfate. After concentration, the product was recrystallized from ethyl acetate/hexanes to provide FMOC—N-hydroxyethylglycine (9.11 g, 92%).

C. Reaction 9

The product (805 mg, 2.36 mmol) was dissolved in MeOH and the solution acidified with a few drops of H$_2$SO$_4$. The solution was heated at reflux for 30 minutes, until TLC indicated a complete conversion to product. Water was added, and the solution extracted with ether, ethyl acetate, and methylene chloride. The ether and ethyl acetate solutions were combined and washed with water and brine, and dried over sodium sulfate. The methylene chloride extract was washed with water and dried. The combined organic layers were concentrated to 880 mg of product, which was used without further purification. This product was dissolved in methylene chloride (11 mL) and cooled in a dry ice bath. Isobutylene (about 10 mL) was added, followed by concentrated sulfuric acid (100 μL). The flask was stoppered and allowed to stand at room temperature. After one week, the flask was cooled to −78° C. opened and allowed to warm up to room temperature under a stream of nitrogen. The methylene chloride solution was washed with sodium carbonate and water, and dried over sodium sulfate. The concentrated material was chromatographed using ethyl acetate/hexanes to provide two major products; by NMR, the desired product and the bis t-butyl product.

The desired product (521 mg, 1.27 mmol) was suspended in 0.1 M sodium phosphate (pH 8.0). Porcine liver esterase (100 μL, 108.5 u/mg, 10 mg/mL) was added followed by Triton® (200 μL, 10% aqueous solution). The pH was maintained at 8 by periodic addition of NaOH. After one day, the solution was extracted with ethyl acetate. TLC indicated a slower moving compound in addition to unreacted starting material, which was verified as FMOC—N-(2-t-butoxyethyl)glycine by NMR. This monomer may be used in peptoids at any position at which a hydroxy-containing side chain is desired.

Example 5

FMOC—N-carboxymethyl(t-butyl Ester)glycine

A. Reaction 10

Glycine, t-butyl ester (10.0 g, 52.3 mmol) was dissolved in water (150 mL) and the pH adjusted to 9.5 with NaOH. Chloroacetic acid (1.1 g, 11.6 mmol) in 50 mL water was added dropwise to the solution with stirring while maintaining the pH with a pH stat. After the addition was complete, the reaction was allowed to stir overnight. The basic solution was exhaustively extracted with EtOAc and CH$_2$Cl$_2$ until there was no additional glycine t-butyl ester in the aqueous layer, as judged by TLC. The material was used without further purification.

B. Reaction 11

The pH of the solution was adjusted to 9.5, and acetone (100 mL) added. A solution of FMOC—NHS (4.0 g, 11.9 mmol) in acetone (50 mL) was added slowly and the pH maintained at 9.5. After stirring 2 days, the basic solution was extracted with ether, cooled in an ice bath, and carefully acidified to pH 2.5 with KHSO$_4$. The acidic solution was extracted with ethyl acetate. The organic layer was washed with water and dried over sodium sulfate. After concentration, FMOC—N-carboxymethyl(t-butyl ester)glycine (3.07 g, 64% from chloroacetic acid) was obtained as an oil. This monomer may be used in peptoids at any position at which an acidic side chain is desired.

Example 6

Preparation of Peptoids

Di- and tri-peptoids containing 1–3 N-substituted glycine analogs of the invention were prepared using the N-substituted amino acids FMOC—N-isobutylglycine (Leu*) and FMOC—N-benzylglycine (Phe*). The amino acids were loaded onto a Wang resin (S. -S. Wang, J Am Chem Soc (1973) 95:1328) and coupled using benzotriazoyloxy-tris (dimethylamino)phosphonium hexafluorophosphate (BOP) and diisopropylethylamine (DIEA). Substitution levels were determined using standard analytical procedures by quantifying the amount of FMOC released by treatment with piperidine in DMF. These resins are routinely capped with benzoyl chloride/pyridine prior to further coupling reactions.

HPLC analysis was performed using a Hewlett-Packard Diode-Array 1090 Liquid Chromatograph, using a 2% gradient of 0–100% acetonitrile (0.1% trifluoroacetic acid)/$H_2O$ (0.1% TFA) over 50 minutes, with an initial 5 min delay (flow rate 0.8 mL/min). The column used was a 40 mm××25 cm Vydac® C-18 stainless steel column. IR spectra were obtained using a Nicolet FT-IR. FMOC-amino acids, loaded resin, and BOP were obtained from Advanced Chemtech.

(A) FMOC-Leu*-Cl was prepared by dissolving FMOC—N-isobutylglycine (150 mg, 0.42 mmol) in $CH_2Cl_2$ (2.8 mL), and adding thionyl chloride (309 μL, 4.2 mmol) and 3 μL DMF (0.04 mmol). The reaction mixture was stirred for 5 hours and concentrated in vacuo., repeatedly dissolving in $CH_2Cl_2$ (3××) to provide FMOC-Leu*-Cl as a colorless oil (146 mg. 92%): IR ($cm^{-1}$)-1804, 1720, 1715. FMOC-Phe*-Cl was similarly prepared.

(B) The Wang resin (0.94 mmol/g, Applied Biosystems, Inc.) was loaded by combining FMOC-Phe* (0.8 mmol) with Wang resin (325 mg, 0.3 mmol) in $CH_2Cl_2$ (4.5 mL). BOP (267 mg, 0.6 mmol) was added and dissolved, followed by DEEA (265 μL. 1.5 mmol). The resulting slurry was stirred at 23° C. for 24 hours. The resin was then filtered and washed with $CH_2Cl_2$ and 40% MeOH/$CH_2Cl_2$, and dried under vacuum. The resin was then capped by swelling with $CH_2Cl_2$ (4.3 mL) and cooled to 0° C. Pyridine (120 μL) was added followed by benzoyl chloride (140 μL). The resin was stirred while warming to 23° C. over 1 hour, filtered and washed with $CH_2Cl_2$ and dried under vacuum to provide FMOC-Phe*-Wang.

(C) Similarly, proceeding as in part (B) above but substituting FMOC—N-isobutylglycine, FMOC—N-(N'-BOC-2-aminoethyl)glycine, FMOC—N-(2-t-butoxyethyl)glycine, or FMOC—N-carboxymethyl(t-butyl ester)glycine for FMOC—N-benzylglycine, the corresponding resins are prepared.

(D) FMOC-Phe*-Wang resin (63 mg, 0.43 mmol/g) was deprotected by initial washing with 20% piperidine in DMF, followed by treatment for 20 min. After repeatedly washing with DMF, MeOH, and $CH_2CL_2$, the resin was treated with FMOC-Leu*-Cl (30 mg, 0.08 mmol) in $CH_2Cl_2$ (380 μL). Pyridine (110 μL, 1.4 mmol) was added, and the resin shaken for 4 hours. Monitoring the coupling (A. Grandas et al., Int J Peptide Protein Res (1989) 33.386–90) revealed that the reaction was complete within 20 min. Filtration and washing with $CH_2Cl_2$ and MeOH provided the fully coupled resin FMOC-Leu*-Phe*-Wang, (E) Similarly, proceeding as in parts (B-D) above, the following resins (and their deprotected forms) were prepared:

FMOC-Leu*-Pro-Wang; FMOC-Leu*-Leu*-Wang; FMOC-Leu*-Leu-Wang; FMOC-Phe*-Phe*-Wang; FMOC-Gly-Leu*-Wang; FMOC-Leu*-Phe-Wang; and FMOC-Leu*-Leu-Phe-Wang.

Leu* indicates N-isobutylglycine, and Phe* indicates N-benzylglycine. The peptoids are cleaved from the resins using 95% TFA, while the reaction was monitored by RP-HPLC as described above. The results are shown in Table 3 as follows:

TABLE 3

Peptoids and Retention Times

| Peptoid | Retention Time (min) |
|---|---|
| FMOC-Leu* | 38.7 |
| Leu* | (not retained) |
| FMOC-Phe* | 39.3 |
| Phe* | 15.0 |
| FMOC-Leu*-Leu* | 40.1 |
| Leu*-Leu* | 19.7 |
| FMOC-Leu*-Phe* | 41.1 |
| FMOC-Phe*-Phe* | 43.4 |
| FMOC-Leu*-Leu | 40.4 |
| Leu*-Leu | 21.9 |

Example 7

Solid Phase Chemistry

Resins: Unloaded WANG (HMP) resin, Rink resin, and preloaded PAM resins were bought from Advanced Chemtech or ABI. The first amino acid was coupled to the WANG and Rink resins using the PyBrop method described below.

Resin Deprotection: The resin was treated with a 20% piperidine in DMF solution for one minute, drained, and repeated for 20 m. After draining, the resin was washed with DMF 3 times and methylene chloride 5–7 times.

Substitution Level: A preweighed dried amount of resin is treated with a solution of 20% piperidine in DMF ($300\lambda^{-1}$ mL) in an eppendorf tube on a vortexer. After 20–30 m, the tubes are centrifuged for a few minutes to settle the resin. An aliquot is removed (50λ) and diluted to 1 mL with acetonitrile. The absorbance at 300 nm is recorded vs. a standard of the same dilution pip/DMF in ACN. In general, the spectrum from 280–320 nm is taken to ensure the characteristic pattern for an FMOC derived product. The following formula is used to calculate the mmol/g (substitution level) of the resin: mmol/g=[Abs(300 nm)][λpip/DMF solution] [ACN dilution]/[mg resin][$\in M^{-1}cm^{-1}$][1 cm], e.g., 1.47 mg resin, $A_{300}$=0.298, 0.5 mL pip/DMF used, 50/1000 dilution.

Coupling: Acyl halide chemistry: The amino acid (1 mmol) was dissolved in methylene chloride (10 mL) and treated with thionyl chloride (750λ) and DMF (10λ). The reaction was monitored by TLC or HPLC by mixing 10λ with 100λ methanol. In all cases studied, the $R_f$ of the methyl ester was greater than the corresponding $R_f$ of the carboxylic acid. After stirring 30 m to 2 h, the solution was concentrated on a rotavap several times from methylene chloride, and benzene or toluene, followed by high vacuum concentration to remove the solvents. In general, the compounds were oils, and often colored yellow to brown. They were used without further purification. The acyl halide was dissolved in an appropriate amount of methylene chloride and was added to the deprotected resin, followed by a solution of DIEA/ methylene chloride. After an appropriate time, usually 1 hour, the resin was drained and washed well with methylene chloride, dried, and assayed for FMOC content.

Coupling: PyBroP chemistry: The resin (~100 mg, 0.05 mmol), after deprotection, was washed well (5–10 times) with methylene chloride. A 0.2 mmol aliquot of the amino acid was weighted into a vial. This was dissolved in 1.0 mL methylene chloride and 0.1 mL DIEA. A 0.2 mmol aliquot of PyBroP (bromo-tris-pyrrolidino-phosphonium hexafluoro-phosphate), purchased from Nova chemicals UK, was weighted into another vial. It was also dissolved in 1.0 mL methylene chloride, however, this solution remained cloudy. The amino acid solution was added to the resin followed by the PyBroP solution. The mini-column was capped, vented, and gently shaken for one hour. The resin was drained, washed well with methylene chloride and ready for a repeat coupling or capping.

Coupling: DIC/HOBt chemistry: The resin (~50 mg, 0.033 mmol), after deprotection was washed well (5–10 times) with DMF. To the resin was added 440λ of DMF followed by 170λ of a 1M solution of amino acid in DMF and 170λ. of a 1M solution of DIC and HOBt in DMF. The mini-column was capped, vented, and gently shaken for one hour. The resin was drained, washed well with methylene chloride and ready for a repeat coupling or capping.

Capping: After coupling, the resin was washed well with methylene chloride and treated with 100λ acetic anhydride, 100λ pyridine, and 2 mL methylene chloride for 30 minutes.

Example 8

Polymer Purification and Analysis

Polymers using WANG Resin: Polymers prepared using the WANG or RINK resins were cleaved using the standard protocol, i.e., 95% aqueous TFA for one hour at room temperature. No scavengers were necessary (no Trp, Tyr, Met). The TFA solution was filtered, dried down, and resuspended in 20% aqueous acetic acid for HPLC analysis.

Polymers using PAM Resin: Resins were cleaved in HF at 0° C. for one hour. Either the resin was extracted with DMF, or the resin was extracted with 50% aqueous acetic acid, concentrated, and redissolved in acetonitrile for HPLC analysis. In both cases, the organic solvent was diluted to approximately 25% with water before reversed phase HPLC on C-18 support.

The following examples are used to assay for the ability of AV peptoids to interact with and preferably inhibit the activity of an Inhibitor of Apoptosis protein (IAP), as measured by IAP binding, procaspase-3 activation or promotion of apoptosis. Note that these assays may be used to assay peptoids for requisite IAP binding as well as to screen for agents (e.g. antagonists) which potentiate peptoid-IAP binding. The in vitro binding and FP assays (Examples 9–11) are particularly suited to identify peptoid antagonists, i.e. compounds which competitively displace the peptoid, preferably at at least 1%, more preferably at at least 10%, more preferably at at least 50%, and most preferably in excess, of equimolar displacement. Accordingly, the invention provides such AV peptoid antagonists produced (i.e. initially identified through) by these methods.

Example 9

In Vitro IAP (BIR) Binding/Interaction Assay

Interaction between AV peptoids and IAPs was examined by GST-mediated pull-down assays. Approximately 0.4 mg of a recombinant IAP fragment (second BIR (baculoviral IAP repeat) motif of XIAP) was bound to 200 ml of glutathione resin as a GST-fusion protein and incubated with 0.5 mg of radiolabeled AV peptoids at room temperature. After extensive washing with an assay buffer containing 25 mM Tris, pH 8.0, 150 mM NaCl, and 2 mM dithiothreitol (DTT), the complex was eluted with 5 mM reduced glutathione and visualized by SDS-PAGE with Coomassie staining. AV peptoids are shown to specifically bind the IAP.

In particular experiments, we demonstrate that wild-type N-terminal Smac fragments are sufficient to effect IAP binding. Smac stimulates activation of procaspase-3 by relieving the IAP inhibition[20, 21]. All members of the IAP family contain at least one BIR (baculoviral IAP repeat) motif and many contain three[9]. Recent experiments indicate that different BIR domains may exhibit distinct functions; for example, the second BIR domain (BIR2) of XIAP appears to be a potent suppressor of apoptosis and a direct inhibitor for caspases whereas neither BIR1 nor BIR3 exhibited similar activity[23]. We report here that Smac and N-terminal fragments thereof can specifically interact with the second or third BIR domain of XIAP. Similar results are obtained with N-terminal fragments of Smac homologs. Reaper, Grim, and Hid, as well as synthetic homologs; see Table 4.

TABLE 4

IAP binding of AV peptoids comprising wild-type Smac, Reaper, Grim and Hid N-terminal peptide sequences and synthetic homologs.

| AV Peptoid | IAP Binding | AV Peptoid | IAP Binding |
|---|---|---|---|
| Smac-2: NH2-AV-COOH | ++ | Grim-3: NH2-AIA-COOH | +++ |
| Smac-3: NH2-AVP-COOH | +++ | Grim-4: NH2-AIAY-COOH (SEQ ID NO:13) | +++ |
| Smac-4: NH2-AVPI-COOH (SEQ ID NO:5) | +++ | Grim-5: NH2-AIAYF-COOH (SEQ ID NO:14) | +++ |
| Smac-5: NH2-AVPIA-COOH (SEQ ID NO:6) | +++ | Hid-4: NH2-AVPF-COOH (SEQ ID NO:15) | +++ |
| Smac-6: NH2-AVPIAQ-COOH (SEQ ID NO:7) | +++ | Hid-5: NH2-AVAFY-COOH (SEQ ID NO:11) | +++ |
| Smac-7: NH2-AVPIAQK-COOH (SEQ ID NO:8) | +++ | Hid-6: NH2-AVAFYL-COOH (SEQ ID NO:16) | +++ |

TABLE 4-continued

IAP binding of AV peptoids comprising wild-type Smac, Reaper,
Grim and Hid N-terminal peptide sequences and synthetic homologs.

| AV Peptoid | IAP Binding | AV Peptoid | IAP Binding |
|---|---|---|---|
| Smac-7R: NH2-KQAIPVA-COOH (SEQ ID NO:9) | 0 | Synth-3A: NH2-AIP-COOH | +++ |
| Reaper-3: NH2-AVA-COOH | +++ | Synth-3B: NH2-ALP-COOH | +++ |
| Reaper-4: NH2-AVAF-COOH (SEQ ID NO:10) | +++ | Synth-3C: NH2-ALA-COOH | +++ |
| Reaper-5: NH2-AVAFY-COOH (SEQ ID NO:11) | +++ | Synth-3D: NH2-ALV-COOH | +++ |
| Reaper-6: NH2-AVAFYI-COOH (SEQ ID NO:12) | +++ | Synth-3E: NH2-AVV-COOH | ++ |

Example 10

High-Throughput In Vitro Fluorescence Polarization Binding Assay

Sensor: Rhodamine-labeled AV peptoid (final conc.=1–5 nM)
Receptor: Glutathione-S-transferase/BIR fusion protein (final conc.=100–200 nM)
Buffer: 10 mM HEPES, 10 mM NaCl, 6 mM magnesium chloride, pH 7.6
1. Add 90 microliters of peptoid/BIR mixture to each well of a 96-well microtiter plate.
2. Add 10 microliters of test compound per well.
3. Shake 5 min and within 5 minutes determine amount of fluorescence polarization by using a Fluorolite FPM-2 Fluorescence Polarization Microtiter System (Dynatech Laboratories, Inc).

Tested AV peptoids and Smac fragments (except 7R) significantly and specifically bind the IAP BIR domain, see Table 5 as follows:

11. High Throughput Solid Phase Peptoid-BIR Binding/Binding-Interference Assay

A. Reagents:
Neutralite Avidin: 20 µg/ml in PBS.
Blocking buffer: 5% BSA, 0.5% Tween 20 in PBS; 1 hour at room temperature.
Assay Buffer: 100 mM KCl, 20 mM HEPES pH 7.6, 1 mM MgCl$_2$, 1% glycerol. 0.5% NP-40, 50 mM b-mercaptoethanol, 1 mg/ml BSA, cocktail of protease inhibitors.
$^{33}$P Smac peptoid 10× stock: $10^{-8}$–$10^{-6}$M "cold" peptide mimetic supplemented with 200,000–250,000 cpm of labeled mimetic (Beckman counter). Place in the 4° C. microfridge during screening.
Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2mM NaVO$_3$ (Sigma #S-6508) in 10 ml of PBS.
BIR: $10^{-7}$–$10^{-5}$ M biotinylated BIR domain (supra) in PBS.

TABLE 5

AV Peptoids Effecting IAP Binding and Test Compounds
Demonstrating Peptoid Displacement (Antagonists).

| AV Peptoid* | IAP Binding | Test Compounds** demonstrating displacement | Displacement |
|---|---|---|---|
| XWBC2411 | +++ | N67218, N63439, S25539, S57739, S43643 | +++ |
| XWBC0093 | +++ | N32665, N19093, N37883, S38674, S03480 | +++ |
| CDWB4558 | +++ | C32829, C10438, C85376, C26347, C46792 | +++ |
| WYRMS7726 | +++ | N47639, N27374, S29387, S68093, C62039 | +++ |
| WYRMS1592 | +++ | S89374, S26293, S10328, S72934, C39384 | +++ |
| WYRMS9311 | +++ | N28474, S26743, C29287, C27478, C32937 | +++ |
| TOKA0283 | +++ | S29374, S07984, S28340, S14242, C86908 | +++ |
| TOKA6305 | +++ | N16261, S21652, S15533, S46658, S93399 | +++ |
| TOKA3375 | +++ | S37355, S79685, S76246, S97421, S14243 | +++ |
| BAKHC7539 | +++ | S32532, C09485, C36389, C54200, C15437 | +++ |
| BAKHC2294 | +++ | N36536, N94777, S32520, S36378, C21233 | +++ |
| BAKHC5275 | +++ | S59273, S32688, S29875, S78993, C20357 | +++ |

*Mimetics with BC designations are made by the backbone cyclic proteinomimetic protocol (Kasher et al., 1999, supra); mimetics with RMS designations are made by the rigid molecular scaffold protocol (Andrade-Gordon et al., 1999, supra); mimetics with KA and KHC designations are made by the α-ketoamide and α-ketoheterocyycle protocols (Boatman et al., 1999, supra), respectively.
**Test compounds with N, C and S designations are obtained from natural (Merck & Co. Inc.), combinatorial (DuPont Pharmaceuticals Co.) and other synthetic libraries (Pangea Systems), respectively.

B. Preparation of assay plates:
  Coat with 120 μl of stock N-Avidin per well overnight at 4° C.
  Wash 2 times with 200 μl PBS.
  Block with 150 μl of blocking buffer.
  Wash 2 times with 200 μl PBS.

C. Assay:
  Add 40 μl assay buffer/well.
  Add 10 μl compound or extract.
  Add 10 μl $^{33}$P-peptoid (20–25,000 cpm/0.1–10 pmoles/well=$10^{-9}$–$10^{-7}$ M final conc).
  Shake at 25° C. for 15 minutes.
  Incubate additional 45 minutes at 25° C.
  Add 40 μM biotinylated BIR (0.1–10 pmoles/40 ul in assay buffer)
  Incubate 1 hour at room temperature.
  Stop the reaction by washing 4 times with 200 μM PBS.
  Add 150 μM scintillation cocktail.
  Count in Topcount.

D. Controls for all assays (located on each plate):
  a. Non-specific binding
  b. Soluble (non-biotinylated BIR) at 80% inhibition AV peptoids and Smac fragments (except 7R) significantly and specifically bind the IAP BIR domain.

Example 12

Hela Cell Extracts: Radiolabeled Procaspase-3 Activation Assay.

20 mg S-100 extracts of HeLa cells were incubated alone (Control), or with AV peptoids (50 nM) nM, or with 30–1000 mM of N-terminal Smac peptides in different lengths. The reactions were carried out with the addition of 1 mM dATP, 1 mM additional MgCl2, 0.2 mg/ml horse heart cytochrome c, and 1 ml of in vitro translated, $^{35}$S-labeled caspase-3 in a final volume of 20 ml. The reaction mixtures were incubated at 30° C. for 1 hr followed by electrophoresis on a 15% PAGE gel. The gel was subsequently transferred onto a nitrocellulose filter and exposed to a phosphoimaging cassette. All AV peptoids and Smac fragments significantly promoted activation of procaspase-3, whereas negative control Smac-7R did not.

Example 13

Hela Cell Extracts: Spectrofluorometric Procaspase-3 Activation Assay.

Human Hela S3 cells were cultured in 150-mm tissue culture dishes in DMEM medium (Dulbecco's modified eagle's medium containing 100 U/ml of penicillin and 100 ug/ml of streptomycin sulfate) supplemented with 10% (v/v) fetal calf serum, and grown in monolayer at 37° C. in an atmosphere of 5% $CO_2$. Cells at 70% confluence were washed once with 1×phosphate-buffered saline (PBS) and harvested by centrifugation at 800×g for 5 min at 4° C. The cell pellets were resuspended in 3 volume of Buffer A (20 mM Hepes-KOH. pH 7.5, 10 mM, KCL, 1.5 mM MgCl2, 1 mM sodium EDTA, 1 mM sodium EGTA, 1 mM DTT, and 0.1 mM PMSF) and cell extracts were prepared as described in Liu et al.(24). Human c-IAP-1 or c-IAP-2, or XIAP either full length of truncated proteins that contain the first three BIR domain, or the second, or third BIR domain are added to the HeLa cell extracts and the caspase activation reaction is started by adding 1 mM dATP and 300 nM cytochrome c. The caspase-3 activity is measured by spectrofluorometric assay as previously described by MacFarlane et al.(1997, J. Cell Biol. 137, 469–479). Aliquots of 8 mg of S-100 prepared as in Liu et al. were assayed in 96-well microtiter format in a 150 ml of reaction containing 0.1 mM Hepes, PH 7.4, 2 mM DTT, 0.1% (w/v) Chaps, and 1% (w/v) Sucrose. The reactions were started by adding caspase specific fluorogenic substrate benzyloxycarbonyl-Asp-Glu-Val-Asp-7-amino-4-trifluoromethylcoumarin-Z-DEVD-A FC (commercially available from Enzyme Systems) to the final concentration of 20 mM and continued at 37° C. for 30 min. Liberation of AFC from the substrates was monitored continuously using excitation/emission wavelenth paires of 400/505 nm. AV peptoids and Smac fragments (except 7R) significantly promoted activation of procaspase-3.

Example 14

Reconstituted Recombinant Radiolabeled Procaspase-3 Activation Assay

AV peptoids and N-terminal Smac peptides (30–3000 mM) were incubated with recombinant human Apaf-1 (40 nM), recombinant human procaspase-9 (2 nM), purified horse heart cytochrome c (nM) and mouse XIAP (70 nM) in the presence of 1 mM dATP, 1 mM $MgCl_2$ and 1 ml of in vitro translated, $^{35}$S-labeled caspase-3 in a final volume of 20 ml. The reaction mixtures were incubated at 30° C. for 1 hr followed by electrophoresis on a 15% PAGE gel. The gel was transferred onto a nitrocellulose filter and exposed to a phosphoimaging cassette. Active Smac protein (50 nM) and an inactive peptide Smac-7R (3000 mM) are also included as controls. All AV peptoids and Smac fragments (except 7R) significantly promoted activation of procaspase-3.

Example 15

Reconstituted Recombinant Spectrofluorometric Procaspase-3 Activation Assay

A reconstituted recombinant procaspase-3 activation system is constructed as described above except the human caspase-3 is produced from bacterial expression as described in Liu et al., 1997 (supra) and is not labeled. The caspase-3 activity is measured by spectrofluorometric assay as previously described by MacFarlane et al. (1997, J. Cell Biol. 137, 469–479). Aliquots of 8 mg of S-100 prepared as above were assayed in 96-well microtiter format in a 150 ml of reaction containing 0.1 mM Hepes, PH 7.4, 2 mM DTT, 0.1% (w/v) Chaps, and 1% (w/v) Sucrose. The reactions were started by adding caspase specific fluorogenic substrate benzyloxycarbonyl-Asp-Glu-Val-Asp-7-amino-4-trifluoromethylcoumarin-Z-DEVD-A FC (SEQ ID NO: 17) (commercially available from Enzyme Systems) to the final concentration of 20 mM and continued at 37° C. for 30 min. Liberation of AFC from the substrates was monitored continuously using excitation/emission wavelenth paires of 400/505 nm. AV peptoids and Smac fragments (except 7R) significantly promoted activation of procaspase-3.

Example 16

Cell-Based Assay: Smac Peptides Potentiate Apoptosis Induced by UV or Etoposide in Cultured HeLa Cells $0.75 \times 10^5$ of HeLa-S cells/well were plated in 48-well tissue culture plate. Cells were incubated with 1 mM inactive Smac peptide (Smac-7R, NH2-KQAIPVA-COOH, SEQ ID NO:9) or with 1 mM N-terminal 4-amino acid Smac peptide (Smac-4, NH2-AVPI—COOH. SEQ ID NO:5), with selected AV peptoids comprising peptide mimetics, or with vehicle only (Control) for 12 hr. The cells were then treated with either 320,000 microjoules of UV irradiation using a Stratalinker or with 100 mM chemotherapeutic Etoposide. Cells were then stained with 1 mg/ml Hoechst 33342 dye at different time points and apoptotic cells were counted as those with condensed nuclear chromatin under a fluorescent microscopy. AV peptoids, including Smac peptides, showed significant increases in apoptotic induction at 2, 4 and 6 hrs (for UV insult) and at 10 and 20 hr (for etoposide); see, e.g. Table 6, below.

TABLE 6

AV Peptoids and AV peptoid Antagonists (Example 10) Shown to Enhance Apoptosis.

| AV Peptoid | Apoptosis | Antagonists | Apoptosis |
|---|---|---|---|
| XWBC2411 | +++ | N67218, N63439, S25539, S57739, S43643 | +++ |
| XWBC0093 | +++ | N32665, N19093, N37883, S38674, S03480 | +++ |
| CDWB4558 | +++ | C32829, C10438, C85376, C26347, C46792 | +++ |
| WYRMS7726 | +++ | N47639, N27374, S29387, S68093, C62039 | +++ |
| WYRMS1592 | +++ | S89374, S26293, S10328, S72934, C39384 | +++ |
| WYRMS9311 | +++ | N28474, S26743, C29287, C27478, C32937 | +++ |
| TOKA0283 | +++ | S29374, S07984, S28340, S14242, C86908 | +++ |
| TOKA6305 | +++ | N16261, S21652, S15533, S46658, S93399 | +++ |
| TOKA3375 | +++ | S37355, S79685, S76246, S97421, S14243 | +++ |
| BAKHC7539 | +++ | S32532, C09485, C36389, C54200, C15437 | +++ |
| BAKHC2294 | +++ | N36536, N94777, S32520, S36378, C21233 | +++ |
| BAKHC5275 | +++ | S59273, S32688, S29875, S78993, C20357 | +++ |

Example 17

In Vivo Metastasis Assay

Immunosuppressed mice (athymic nude/nude SCID females from Harlan Sprague Dawley) are housed in autoclaved cages with microisolator tops, and all manipulations of the animals are done in a laminar flow hood after wiping down both the hood, gloves and cages with ABQ sterilant. The mice are fed sterile Pico Lab Chow (Purina) and autoclaved St. Louis tap water. AV peptoids are administered intra-gastrically daily to the mice in sterile water containing 2% carboxymethyl cellulose via sterile, disposable animal feeding needles (Poper & Sons Cat #9921; 20 g×1.5"), seven days a week between 7:00 and 8:00 am. The compounds and control (sterile water plus 2% carboxymethyl cellulose) are kept stored at −80° C. wrapped in aluminum foil to prevent any light induced changes, and each day's supply is thawed just prior to use.

Compounds are tested for their effects on the metastatic potential of C8161 cells injected intravenously via the tail vein: at 40 and 100 mg/kg, compared to the control. The concentration of the compounds in the vials used to give the 100 mg/kg doses are 2.5 times that in the 40 mg/kg dose so that approximately the same volume is used in both cases, approximately 0.5 mL/animal. The experiments start with nine animals per group at day −4. On day zero, $2 \times 10^5$ C8161 cells in cold Hank's Balanced Salt Solution (HBSS) are injected intravenously via tail vein inoculation. The protocol is continued for an additional 24 days, at which time the animals are sacrificed and their lungs removed and fixed in a solution of Bouins/formaldehyde (5 parts: 1 part). Tumors are quantified on the entire surface of the lungs by rotating the lungs and counting the tumors on each lobe using a 6× magnifying glass. Statistical analysis is performed using the statistical package of Microsoft's Excel spreadsheet software.

The effects of test AV peptoid, at two different concentrations, on the metastatic potential of C8161 cells in SCID mice are evaluated: oral gavaging of the animals with tested AV peptoids significantly reduces the number of lung metastases in the SCID mouse population.

Example 18

In Vivo Combination Therapy: B.I.D. & Q.I.D.

The effect of in vivo combination therapy of AV peptoids (20 or 80 mpk/dosing p.o. or i.p.) with chemotherapies paclitaxel (5 or 20 mpk), 5-Fu (50 mpk), vincristine (1 mpk) or cytoxan (100 mpk, BID, ip) on HTB 177 xenografts (NCI—H460, a human lung large cell carcinoma) using two and four times a day dosing is demonstrated in athymic nu/nu female mice, 5–6 weeks old. On Day 0, HTB 177 cells, $3 \times 10^6$, are injected s.c. into the flank of 220 mice and the mice divided into treatment and control groups:

Peptoid was dissolved in 20% hydroxyl-propyl-betacyclodexatrin (Vehicle 1); 0.2 ml of peptoid solution was the dosing volume. Paclitaxel was dissolved in a diluted ethanol/cremophor EL solution (Vehicle II) and the i.p. dosing volume for paclitaxel was 0.1 ml. Cytoxan, 5-FU, and Vincristine were dissolved in sterile water. The 80 mpk dosing peptoid solution is made by adding 17 ml of 20% HPBCD to a 50 ml tube containing 136 mn of peptoid to dissolve. The mixture was sonicated until a complete solution was made. The 20 mpk dosing solution is made by placing 2 ml of the 80 mpk solution into a 15 ml tube, adding 6 ml of 20% HPBCD, and vortexing the solution to mix it.

Tumor cells are inoculated into mice in the morning of Day 0, and the mice weighed, randomized, and ear-marked afterwards. Drug treatment begins at 7:30 am on Day 4. The animals are dosed with peptoid or vehicle I solution, at 7:30 am, and 7:30 pm, 7 days a week. Tumor growth is quantitated by measuring tumor volume on Day 7 and Day 14. Both peptoid and chemotherapies demonstrate inhibition; combination therapies provide enhanced inhibition over either therapy alone.

Example 19

In Vivo Therapy in the WAP-RAS Transgenic Model

Peptoid and Paclitaxel combination efficacy is also evaluated in the Wap-ras transgenic model. This model is used in a therapeutic mode in which treatments are initiated after mice had well developed tumors.

Peptoid (20 mpk/dosing po) was dissolved in 20% hydroxyl-propyl-betacyclodexatrin (Vehicle 1). 0.2 ml of peptoid solution is the oral dosing volume. Paclitaxel (5 mpk/dosing ip) was dissolved in a diluted ethanol/cremophor EL solution (vehicle II) and the i.p. dosing volume for paclitaxel was 0.1 ml.

The mice are weighed, randomized, and ear-marked on Day 0. Peptoid treatment and Vehicle I treatment began on Day 1 and continued every 12 hours until Day 21. Paclitaxel and Vehicle II treatments are started on Day 4 and continued daily on Day 5, 6, and 7. Wap-ras tumors do not respond to treatment with Paclitaxel but do respond to peptoid treatment at 20 mpk alone and combined therapy enhanced efficacy.

References

1. Steller, H. *Science* 267, 1445–1449 (1995).
2. Jacobson, M. D., Weil, M. & Raff, M. C. *Cell* 88, 347–354 (1997).
3. Hengartner, M. O.. *Curr. Opin. Genet. Dev.* 6, 34–38 (1996).
4. Horvitz, H. R. *Cancer Res.* 59, 1701–1706 (1999).
5. Thompson, C. B. *Science* 267, 1456–1462 (1995).
6. Green, D. R. & Martin, S. J. *Curr. Opin. Immunol.* 7, 694–703 (1995).
7. Thornberry, N. A. & Lazebnik, Y. *Science* 281, 1312–1316 (1998).
8. Chinnaiyan, A. M. & Dixit, V. M. *Curr. Biol.* 6, 555–562 (1996).
9. Deveraux, Q. L. & Reed, J. C. *Genes Dev.* 13, 239–252 (1999).
10. Miller, L. K. *Trends Cell Biol.* 9, 323–328 (1999).
11. Wang, S., et al. *Cell* 98, 453–463 (1999).
12. Goyal, L., et al. *EMBO J.* 19, 589–597 (2000).
13. Zou, H., Henzel, W. J., Liu, X., Lutschg, A. & Wang, X. *Cell* 90, 405–413 (1997).
14. Li, P., et al.. *Cell* 91, 479–489 (1997).
15. Srinivasula, S. M., et al. *Mol. Cell* 1, 949–957 (1998).
16. Yang, X., Chang, H. Y. & Baltimore, D. *Science* 281, 1355–1357 (1998).
17. Hu, Y., et al.. *J. Biol. Chem.* 273, 33489–33494 (1998).
18. Zou, H., Li, Y., Liu, X. & Wang, X. *J. Biol. Chem.* 274, 11549–11556 (1999).
19. Saleh, A., et al. *J. Biol. Chem.* 274, 17941–17945 (1999).
20. Du, C., Fang, M., Li, Y., Li, L. & Wang, X. *Cell* 102, 33–42 (2000).
21. Verhagen, A., et al.. *Cell* 102, 43–53 (2000).
23. Takahashi, R., et al.. *J. Biol. Chem.* 273, 7787–7790 (1998).
24. Liu, X., Zou, H., Slaughter, C. & Wang, X. *Cell* 89, 175–184 (1997).
25. Liu, X., Kim, C. N., Yang, J., Jemmerson, R. & Wang, X. *Cell* 86 (1996).
26. Tamm, I. et al. Clin Cancer Res 6: 1796–1803 (2000)
27. Kitada, S. et al. Blood 91: 3379–3389 (1998)
28. Wagenknecht, B. et al. Cell Death Differ 6: 370–376 (1999)
29. Tamm, I. et al. Cancer Res 58: 5315–5320 (1998)
30. Chen, Z. et al. Biochem Biophys Res Commun 264: 847–854 (1999)
31. Deveraux, Q. L. et al. EMBO J 17: 2215–2223 (1998)
32. Olie, R. A. et al. Cancer Res 60: 2805–2809 (2000)
33. Tanaka, K. et al. Clin Cancer Res 6: 127–134 (2000)

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A pharmaceutical composition comprising a therapeutically effective amount of an AV peptoid in dosage form and a pharmaceutically acceptable carrier, wherein the peptoid comprises the amino acid sequence Ala-Val-Pro, is fewer than 10 residues in length, has a molecular weight less than 1000, and interacts with an inihibitor of Apoptosis protein (IAP) as measured by IAP binding, wherein:

(a) the peptoid is 3 residues in length;

(b) the peptoid comprises a carbon-carbon or acyl bond in place of a peptide bond;

(c) the peptoid comprises an N-terminus and a C-terminus and peptidyl bonds, wherein one or more of the peptidyl [—C(O)NR—] linkages have been replaced by a non-peptidyl linkage selected from the group consisting of: a —$CH_2$-carbamate linkage [—$CH_2$—OC(O)NR—]; a phosphonate linkage; a —$CH_2$-sulfonamide [—$CH_2$—S(O)$_2$NR—] linkage; a urea [—NHC(O)NH—] linkage; a —$CH_2$-secondary amino linkage; or an alkylated peptidyl linkage [—C(O)NR$^6$—] where R$^6$ is lower alkyl;

(d) the peptoid comprises an N-terminus and a C-terminus and peptidyl bonds, wherein the C terminus is derivatized to —C(O)R$^2$ where R$^2$ is selected from the group consisting of lower alkoxy, and —NR$^3$R$^4$ where R$^3$ and R$^4$ are independently selected from the group consisting of hydrogen and lower alkyl;

(e) the peptoid comprises an N-terminus and a C-terminus and peptidyl bonds wherein: one or more of the —C(O)NH— linkage have been replaced by a linkage selected from the group consisting of a —CR$_2$OC(O)NR-linkage; a phosphonate linkage; a —$CH_2$S(O)$_2$NR— linkage; a —$CH_2$NR— linkage; and a —C(O)NR$^6$-linkage, and a —NHC(O)NH— linkage where R is hydrogen or lower alkyl and R$^6$ is lower alkyl; and the N-terminus is selected from the group consisting of a —NRR$^1$ group; a —NRC(O)R group; a —NRC(O)OR group; a —NRS(O)$_2$R group; a —NHC(O)NHR group; a succinimide group; a benzyloxycarbonyl- NH— group; and a benzyloxycarbonyl- NH— group having from 1 to 3 substituents on the phenyl ring selected from the group consisting of lower alkyl, lower alkoxy, chloro, and bromo, where R and R$^1$ are independently selected from the group consisting of hydrogen and lower alkyl; and the C-terminus has the formula —C(O)R$^2$ where R$^2$ is selected from the group consisting of hydroxy, lower alkoxy, and —NR$^3$R$^4$ where R$^3$ and R$^4$ are independently selected from the group consisting of hydrogen and lower alkyl and where the nitrogen atom of the —NR$^3$R$^4$ group can optionally be the amine group of the N-terminus of the peptide so as to form a cyclic peptide; and physiologically acceptable salts thereof;

(f) the peptoid further comprises an N-substituted glycine analog having the general formula I: X$_n$NRCH$_2$COOX$_c$, wherein R is an amino acid α-substituent and the radicals X$_n$, and X$_c$ are either chains of conventional amino acids, chains of one or more N-substituted glycine analogs, or chains in which conventional amino acids and N-substituted glycine analogs are interspersed; or (g) the peptoid comprises a backbone modification selected from the group consisting of: N-alkylation, α-ester, thioamide, N-hydroxylation, β-ester, sulfonamide, sulfonamide-N, urea, and urethane.

2. The composition of claim 1, further comprising an anti-neoproliferative chemotherapeutic agent other than the AV peptoid.

3. The composition of claim 1, wherein the peptoid has a molecular weight less than 500.

4. The composition of claim 1, wherein the peptoid is 3 to 5 residues in length.

5. The composition of claim 1, wherein the peptoid is 3 residues in length.

6. The composition of claim 1, wherein the peptoid comprises a carbon-carbon or acyl bond in place of a peptide bond.

7. The composition of claim 1, wherein the peptoid comprises an amino-terminal or carboxyl terminal blocking group selected from the group consisting of: t-butyloxycarbonyl, acetyl, alkyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl.

8. The composition of claim 1, wherein the peptoid comprises an N-terminus and a C-terminus and peptidyl bonds, wherein one or more of the peptidyl [—C(O)NR—] linkages have been replaced by a non-peptidyl linkage selected from the group consisting of: a —$CH_2$-carbamate linkage [—$CH_2$—OC(O)NR—]; a phosphonate linkage; a —$CH_2$-sulfonamide [—$CH_2$—S(O)$_2$NR—] linkage; a urea [—NHC(O)NH—] linkage; a —$CH_2$-secondary amine linkage; or an alkylated peptidyl linkage [—C(O)NR$^6$—] where R$^6$ is lower alkyl.

9. The composition of claim 1, wherein the peptoid comprises an N-terminus and a C-terminus and peptidyl bonds, wherein the N-terminus is derivatized to a group selected from the group consisting of: a —NRR$^1$ group; a —NRC(O)R group; a —NRC(O)OR group; a —NRS(O)$_2$R group; a —NHC(O)NHR group, where R and R$^1$ are hydrogen or lower alkyl with the proviso that R and R$^1$ are not both hydrogen; to a succinimide group; a benzyloxycarbonyl- NH—(CBZ- NH—) group; and a benzyloxycarbonyl-NE— group having from 1 to 3 substituents on the phenyl ring selected from the group consisting of lower alkyl, lower alkoxy, chloro, and bromo.

10. The composition of claim 1, wherein the peptoid comprises an N-terminus and a C-terminus and peptidyl bonds, wherein the C-terminus is derivatized to —C(O)R$^2$ where R$^2$ is selected from the group consisting of lower alkoxy, and —NR$^3$R$^4$ where R$^3$ and R$^4$ are independently selected from the group consisting of hydrogen and lower alkyl.

11. The composition of claim 1, wherein the peptoid comprises an N-terminus and a C-terminus and peptidyl bonds wherein:
one or more of the —C(O)NH— linkage have been replaced by a linkage selected from the group consisting of a —CR$_2$-OC(O)NR-linkage; a phosphonate linkage; a —CH$_2$S(O)$_2$NR— linkage; a —CH$_2$ NR— linkage; and a —C(O)NR$^6$-linkage, and a —NHC(O)NH— linkage where R is hydrogen or lower alkyl and R$^6$ is lower alkyl,
and the N-terminus is selected from the group consisting of a —NRR$^1$ group; a —NRC(O)R group; a —NRC(O)OR group; a —NRS(O)$_2$R group; a —NHC(O)NHR group; a succinimide group; a benzyloxycarbonyl- NH— group; and a benzyloxycarbonyl- NH— group having from 1 to 3 substituents on the phenyl ring selected from the group consisting of lower alkyl, lower alkoxy, chloro, and bromo, where R and R$^1$ are independently selected from the group consisting of hydrogen and lower alkyl,
and the C-terminus has the formula —C(O)R$^2$ where R$^2$ is selected from the group consisting of hydroxy, lower alkoxy, and —NR$^3$R$^4$ where R$^3$ and R$^4$ are independently selected from the group consisting of hydrogen and lower alkyl and where the nitrogen atom of the —NR$^3$R$^4$ group can optionally be the amine group of the N-terminus of the peptide so as to form a cyclic peptide,
and physiologically acceptable salts thereof.

12. The composition of claim 1, wherein the peptoid further comprises an N-substituted glycine analog having the general formula I: X$_n$NRCH$_2$COOX$_c$, wherein R is an amino acid α-substituent and the radicals X$_n$ and X$_c$ are either chains of conventional amino acids, chains of one or more N-substituted glycine analogs, or chains in which conventional amino acids and N-substituted glycine analogs are interspersed.

13. The composition of claim 1, wherein the peptoid further comprises an N-substituted glycine analog having the general formula I: X$_n$NRCH$_2$COOX$_c$, wherein R is an amino acid α-substituent and the radicals X$_n$ and X$_c$ are either chains of conventional amino acids, chains of one or more N-substituted glycine analogs, or chains in which conventional amino acids and N-substituted glycine analogs are interspersed, wherein the N-substituted glycine analogs are selected from the group consisting of glycine analogs in which R is ethyl, prop-1-yl , prop-2-yl, 1-methylprop-1-yl, 2-methylprop- 1-yl, benzyl, 4-hydroxybenzyl, 2-hydroxyethyl, mereaptoethyl, 2-aminoethyl, 3-aminopropyl, 4-aminobutyl, 2-methylthioeth-1-yl, carboxymethyl, 2-carboxyethyl, carbamylmethyl, 2-carbamylethyl, 3-guanidinoprop-1-yl, imidazolylmethyl, or indol-3-yl-ethyl.

14. The composition of claim 1, wherein the peptoid comprises a backbone modification selected from the group consisting of: N-alkylation, α-ester, thioamide, N-hydroxylation, β-ester, sulfonamide, sulfonamide-N, urea, and urethane.

* * * * *

SEQUENCE LISTING

<160> NUMBER OF SEQ ID NOS: 17

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 1

Ala Ile Pro Gly Phe Ser Pro Phe
 1               5

```
<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      Sequence
<220> FEATURE:
<221> NAME/KEY: VARIANT
<222> LOCATION: (5)..(8)
<223> OTHER INFORMATION: Phe is N-benzylglicine variant; Ser is
      N-(2-hydroxyethyl)glycine variant

<400> SEQUENCE: 2

Ala Ile Pro Gly Phe Ser Pro Phe
 1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 3

Ala Leu Phe Met Thr
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      Sequence
<220> FEATURE:
<221> NAME/KEY: VARIANT
<222> LOCATION: (3)..(5)
<223> OTHER INFORMATION: Phe is N-benzylglicine variant; Ser is
      N-(2-hydroxyethyl)glycine variant

<400> SEQUENCE: 4

Ala Leu Phe Met Ser
 1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 5

Ala Val Pro Ile
 1

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 6

Ala Val Pro Ile Ala
```

```
<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 7

Ala Val Pro Ile Ala Gln
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 8

Ala Val Pro Ile Ala Gln Lys
  1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 9

Lys Gln Ala Ile Pro Val Ala
  1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 10

Ala Val Ala Phe
  1

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 11

Ala Val Ala Phe Tyr
  1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
                         Sequence

<400> SEQUENCE: 12

Ala Val Ala Phe Tyr Ile
 1               5

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 13

Ala Ile Ala Tyr
 1

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 14

Ala Ile Ala Tyr Phe
 1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 15

Ala Val Pro Phe
 1

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 16

Ala Val Ala Phe Tyr Leu
 1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      Sequence
<220> FEATURE:
<221> NAME/KEY: VARIANT
<222> LOCATION: (1)..(4)
<223> OTHER INFORMATION: Peptide is N-benzyloxycarbonyl,
      C-7-amino-4-trifluoromethylcoumarin variant
```

-continued

```
<400> SEQUENCE: 17

Asp Glu Val Asp
1
```